United States Patent
Buch-Rasmussen et al.

[11] Patent Number: 6,010,485
[45] Date of Patent: Jan. 4, 2000

[54] WORKING CYLINDER

[75] Inventors: Thomas Buch-Rasmussen, Gentofte; Jens Ulrik Poulsen, Virum; Henrik Ljunggreen, Ballerup; Jens Møller Jensen, Copenhagen, all of Denmark

[73] Assignee: Novo Nordisk A/S, Bagsværd, Denmark

[21] Appl. No.: 08/932,354

[22] Filed: Sep. 17, 1997

Related U.S. Application Data

[60] Provisional application No. 60/047,931, May 30, 1997.

[30] Foreign Application Priority Data

Sep. 20, 1996 [DK] Denmark .................................. 1028/96

[51] Int. Cl.⁷ ...................................................... A61M 5/00
[52] U.S. Cl. ............................ 604/191; 604/183; 604/248
[58] Field of Search ..................................... 604/183, 191, 604/207, 246, 236, 247, 248, 256, 221, 226, 228, 30, 32

[56] References Cited

U.S. PATENT DOCUMENTS

| | | |
|---|---|---|
| 3,805,783 | 4/1974 | Ismach . |
| 4,011,685 | 3/1977 | Boyd et al. ........................... 604/183 X |
| 4,740,203 | 4/1988 | Hoskins et al. ........................... 604/191 |
| 5,084,031 | 1/1992 | Todd et al. ............................... 604/248 |
| 5,389,070 | 2/1995 | Morell .................................. 604/183 X |
| 5,439,452 | 8/1995 | McCarty .............................. 604/183 X |
| 5,501,666 | 3/1996 | Spielberg . |
| 5,674,193 | 10/1997 | Hayes .................................... 604/30 X |

FOREIGN PATENT DOCUMENTS

| | | |
|---|---|---|
| 0 188 032 | 7/1986 | European Pat. Off. . |
| 2 106 338 | 9/1971 | Germany . |
| WO 92/10226 | 6/1992 | WIPO . |
| WO 93/20864 | 10/1993 | WIPO . |

*Primary Examiner*—Wynn Wood Coggins
*Assistant Examiner*—A. T. Nguyen
*Attorney, Agent, or Firm*—Steve T. Zelson, Esq.

[57] ABSTRACT

The present invention relates to a drug delivery system, comprising a reservoir from which set doses are apportioned, a dose setting mechanism by which the relative position of two elements is changed by a distance proportional to a set dose, and a push button by activation of which an element is moved a distance corresponding to the distance proportional to the set dose, further comprises a working cylinder having an open end into which a plunger fits, and a closed end at which an inlet and an outlet port connect the space beneath the plunger with an inlet communicating with the reservoir and an outlet communicating with a drug delivery member, respectively. Valves means at the inlet and outlet control the passages from the reservoir to the working cylinder and from the working cylinder to the drug delivery member, respectively. The cylinder with the plunger, and the injection member are independently exchangeable, disposable parts.

4 Claims, 1 Drawing Sheet

WORKING CYLINDER

CROSS-REFERENCE TO RELATED APPLICATIONS

This application claims priority under 35 U.S.C. 119 of Danish application serial No. 1028/96 filed Sep. 20, 1996 and U.S. provisional application Ser. No. 60/047,931 filed on May 30, 1997, the contents of which are fully incorporated herein by reference.

BACKGROUND OF THE INVENTION

1. Field of the Invention

The present invention relates to a drug delivery system comprising
(a) a reservoir from which set doses are apportioned,
(b) a dose setting mechanism by which the relative position of two elements is changed by a distance proportional with a set dose, and
(c) a push button by activation of which an element is moved a distance corresponding to said distance proportional to the set dose.

2. Description of the Related Art

Mainly the dose setting mechanism comprises dose setting elements which are during the setting of a dose displaced relative to each other in such a way that the pressing of the button until it abuts a stop results in a movement of a piston into one end of an cylinder ampoule a distance corresponding to the set dose whereby the dose is pressed out through a needle mounted at the other end of the ampoule.

An example of such an injection device is described in EP 327 910 wherein during the dose setting a nut mounted on a threaded piston rod is screwed along this piston rod away from a stop, and a button mounted on the nut is lifted up over a proximal end of the housing of the device. When the button is pressed to bring the nut back to abutment with the stop, the piston rod is forced into an ampoule a distance corresponding to the set dose.

Such injection devices have shown to be advantageous as the reservoir may content sufficient medicine for say one week and the handling of vials and disposable syringes or syringes which has to be cleaned after each use is avoided. The reservoir even though it is used for several injections has the advantage of a disposable device as the piston is only once moved all the way from one end of the ampoule to the other whereafter the ampoule is disposed of.

One of the draw-backs of the injection devices of the above mentioned type is the fact that to accommodate the ampoule and a piston rod which shall be able to force the piston from one end of the ampoule to the other, the device has to have a length which is more than twice the length of the ampoule. This drawback may however be overcome by using a flexible piston rod which may be bent away from the axis of the ampoule immediately behind this ampoule.

Another draw-back is that the piston area is made larger and consequently the movement of the piston have to be smaller to inject a given dose when the ampoule is given a larger diameter to have a larger volume. This again makes it more tricky to perform a precise setting of a dose and inaccuracies due to the elasticity of the piston become more probable. Further the pressure which has to be exerted on the piston rod increases proportionally with the piston area at the same time as a trend toward the use of thinner needles calls for still higher pressures in the injection cylinder formed by the ampoule. Also a wish for the development of injection devices by which the medicine is pressed out as a skin penetrating jet points towards the use of higher pressures in the injection cylinder. This trend was not foreseen by the development of the mainly used ampoule which consequently is not guaranteed to withstand excessive inner pressures.

An object of the invention is to provide an injection device, by which the above mentioned draw-backs are overcome.

SUMMARY OF THE INVENTION

This is obtained by a drug delivery system as mentioned in the opening of this specification, which system according to the invention is characterised in that it further comprises a working cylinder having an open end into which a plunger fits, a closed end at which an inlet and an outlet port connect the space beneath the plunger with an inlet communicating with the reservoir and an outlet communicating with a drug delivery member, and valve means at the inlet and outlet controlling the passages from the reservoir to the working cylinder and from the working cylinder to the drug delivery member respectively.

Such a working cylinder may be dimensioned in accordance with existing wishes as for pressure in the cylinder and stroke of the plunger. The diameter of the bore in the cylinder may be made so that a wanted working pressure in the cylinder may be obtained by exerting a moderate force at the end of the plunger. At the same time the stroke is enlarged so that even by setting small doses the movement of the plunger is recognisable. The maximal stroke of the plunger corresponds to the maximal dose which one may want to inject and the length of the device will have to be about twice this maximal stroke instead of twice the length of the ampoule.

The valves may be so designed that the valve at the inlet to the working cylinder opens and the valve at the outlet closes when the plunger is drawn outwards in the working cylinder and act in the opposite way when the plunger is pressed into the cylinder. A dose is set by drawing outward the plunger a distance enlarging the volume under the piston with a volume corresponding to the wanted dose. When the plunger is drawn outward liquid is sucked from the reservoir through the open valve at the inlet. The valve at the outlet is closed so that air is not sucked in through the injection member which may be an injection needle or a high pressure nozzle for transdermal jet injection. The dose is injected by pressing home the plunger. This may be done by the injection button which may either be connected to the plunger to follow this plunger when it is moved out of the cylinder, or may be a reciprocable button with a fixed stroke which during its stroke abuts the end of the plunger, which end project into the path of the reciprocable injection button a distance corresponding to the set dose.

The cylinder with the inlet, the outlet, the valves, and the plunger acts like a pump pumping the medicine from the reservoir to the injection member and the reservoir may therefor be placed anywhere appropriate in the device independent of the working cylinder. The reservoir need not be an ampoule either, but may be a flexible bag.

In an embodiment of the drug delivery system according to the invention the valves may be formed by a valve surface at the inner end of the plunger co-operating with inlet and outlet ports in the side wall of the cylinder and so controlled that the outlet port is free and the inlet port is covered by said valve surface when the plunger is moved inwards in the cylinder, and the outlet port is covered and the inlet port is free when the plunger is moved outwards in the cylinder.

In addition to this embodiment an overriding mechanism may be provided allowing the plunger to be set in a rotational position wherein the valve surface covers the outlet port and keep the inlet port free during an inward movement of the plunger. This enable the user to return some of the medicine from the cylinder to the reservoir if a too large dose is erroneously set.

The dose may be set by moving the plunger outwards from an innermost position in the cylinder a distance proportional with the dose to be set.

The reservoir, the cylinder with the plunger, and the injection member may be independently exchangeable, disposable parts. The reservoir may be changed when it is empty or if the user want to change to another type of medicine. The cylinder and plunger may be changed frequently before they become too worn to function satisfactorily, and the delivery member which may be a needle or a high pressure jet nozzle may be changed when necessitated, e.g. for sanitary reasons.

As the medicine is stored in the reservoir and only comes into contact with the working cylinder during the injection step the reservoir may be manufactured from a material which stands long time influence of the medicine, whereas the material for the working cylinder may be chosen on the basis of other demands, so as ability of standing high pressures and ability to be formed with high precision.

BRIEF DESCRIPTION OF THE FIGURES

In the following the invention is described with reference to the drawing, wherein FIG. 1 schematically shows an embodiment of a working cylinder according to the invention, and FIG. 2 schematically shows another embodiment of a working cylinder according to the invention.

DETAILED DESCRIPTION OF THE INVENTION

Figure 1:
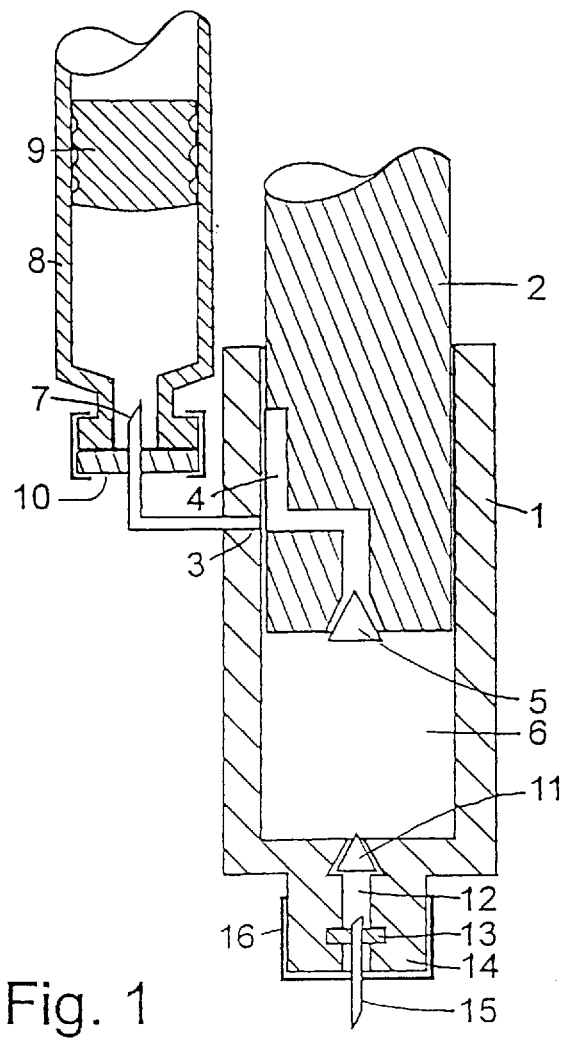

In FIG. 1 is shown a working cylinder 1 in which a plunger 2 may be reciprocated. An inlet 3 is through a cut out 4 in the plunger and an inlet valve 5 connected to an inner space 6 in the cylinder. The inlet is by a tube ending in a pointed needle 7 connected to a reservoir which is here shown as a cylinder ampoule 8. The ampoule is closed by a piston 9 at one end and by a rubber membrane 10 at the other. The needle 7 of the tube leading to the inlet is inserted through the membrane 10 to establish a connection from inside the reservoir to the inner space 6 of the working cylinder 1 when the inlet valve 5 is open.

An outlet is through an outlet valve 11 connected to an outlet channel 12 which is at an outer end closed by a rubber membrane 13. The outer end of the channel through a connecting piece 14 onto which an injecting member is mounted. The injection needle 15 secured in a needle hub 16 which is mounted on the connecting piece 14. The injection member may alternatively a jet nozzle provided on a hub carrying a needle which needle could be inserted through the rubber membrane in the connection piece 14 of the working cylinder 1. Such a jet nozzle may be used as a disposable injection member which is disposed of after use in the same way as it is known by injection needles.

The working cylinder itself may with its valves and connection be used as a disposable device which may be disconnected from the reservoir and the part of a not shown injection device comprising a dose setting mechanism and an injection button. A jet nozzle or a needle may be a part of the cylinder and may be changed with this cylinder after use.

By dose setting, the plunger 2 is drawn outward in the cylinder 1 whereby a subatmospherical pressure is established in the space 6 and liquid is sucked through the open valve 5 and the needle 7 connected to the inlet and the content of the reservoir into said space. When liquid is sucked out of the ampoule 8 the atmospheric pressure will make the piston 9 join the surface of the liquid in said ampoule. Possibly a spring may be provided to exert a weak biasing of the piston 9 inward in the ampoule 8.

The amount of liquid sucked from the ampoule 8 into the space 6 in the working cylinder corresponds to the dose set by drawing outwards the plunger a distance corresponding to the dose wanted. When the plunger is pressed home in the working cylinder the liquid in the space 6 is pressed out through the injecting needle 15 as the valve 5 is closed during this inward movement of the plunger 2 whereas the valve 11 opens the passage from the space 6 to the injection needle 15. The sketched valves 5 and 11 are opened and closed automatically by the pressure differences provided.

Figure 2:
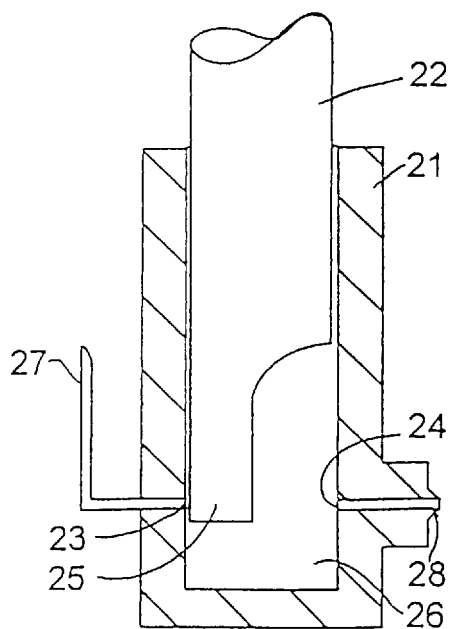

In the embodiment shown in FIG. 2 the valve function is controlled by rotating the plunger 180°. The shown position of the plunger 22 is assumed during injection. The plunger is at its inner end provided with an valve part 25 which in the shown position of the plunger 22 closes an inlet 23 which is through a tube 27 connected to a not shown reservoir. The reservoir may be an ampoule as in FIG. 1 but may as well be a flexible bag a tubing or any other kind of reservoir used for storing liquid medicine. In the shown rotational position of the plunger 22 an outlet 24 is kept open and allow the liquid in the space 26 to be pressed out through said outlet and a jet nozzle 28. The injection member is shown as a jet nozzle mounted directly on the working cylinder 21. However any other kind of injection member may be used without deviating from the scope of the invention. E.g. a connection piece may be provided on which a disposable needles or a disposable jet nozzles may be mounted and changed on request.

A dose is set by drawing the plunger 22 outwards but before this outwards drawing the plunger must be rotated 180° to make the valve part 25 close the outlet 24 and open the inlet 23. The dose is set by controlling the distance the plunger is drawn outwards as a corresponding volume of liquid will be sucked from a reservoir through the tube 27 and into the space 26 beneath the plunger. The set dose is injected by rotating the plunger 22 180° to bring the valve part 25 in the position shown in the figure and pressing the plunger home to press out the liquid under the plunger 22 through the nozzle 28.

If a too large dose is erroneously set, plunger may be moved inward in the cylinder maintained in the rotational position in which the inlet is open and the outlet is closed and thereby the excessive amount of medicine in the cylinder may be pressed back into the reservoir.

It shall be noticed that it is depending on the construction of the not shown injection part of the device whether a needle or a nozzle shall be used as injecting member as jet injection demands an injection part which guarantees a sufficient injection impact on the plunger whereas injection through a needle may be provided by a pressure provided manually whereby the user of the device has a possibility of controlling the injection speed in accordance with his own wishes.

We claim:

1. A drug delivery system comprising:
   a reservoir from which set doses are apportioned;
   a working cylinder having a cylinder wall and open and closed ends;

a plunger having an inner end fitting in said working cylinder, wherein said plunger extends out of said open end and defines, between said inner end and said closed end of said working cylinder, a chamber, and wherein said cylinder wall has inlet and outlet openings communicating with said chamber;

means for connecting said inlet opening and said reservoir for fluid communication therebetween, wherein said plunger can be drawn outwardly relative to said working cylinder to draw a set dose from said reservoir into said chamber, and can be pushed back into said working cylinder to expel the set dose through said outlet opening;

a drug delivery member mounted on said working cylinder so as to be in communication with said outlet opening;

wherein said plunger is rotatable within said working cylinder; and wherein said plunger inner end includes a valve surface which, in a first rotational position of said plunger, blocks said outlet opening but not said inlet opening, and which, in a second rotational position of said plunger, blocks said inlet opening but not said outlet opening, whereby the rotational position of said plunger can be controlled so that said outlet opening is blocked, and said inlet opening is free, when said plunger is moved outwardly relative to said working cylinder to draw a set dose into said chamber, and said outlet opening is free, and said inlet opening is blocked by said valve surface, when the plunger is moved inwardly in said working cylinder to expel the set dose.

2. A drug delivery system according to clam 1, wherein said reservoir, the working cylinder and plunger combination, and said drug delivery member are independent, exchangeable parts.

3. A drug delivery system according to claim 1, wherein said drug delivery member is a high pressure jet nozzle.

4. A drug delivery system according to claim 2, wherein said drug delivery member is a high pressure jet nozzle.

* * * * *